United States Patent
Vedovelli

(10) Patent No.: US 9,216,074 B2
(45) Date of Patent: Dec. 22, 2015

(54) CLEANING OR CARE DEVICE FOR CLEANING OR CARE OF A MEDICAL INSTRUMENT, IN PARTICULAR A DENTAL INSTRUMENT

(75) Inventor: Renzo Vedovelli, Brusaporto (IT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 1104 days.

(21) Appl. No.: 12/717,046

(22) Filed: Mar. 3, 2010

(65) Prior Publication Data

US 2010/0224222 A1    Sep. 9, 2010

(30) Foreign Application Priority Data

Mar. 3, 2009    (EP) .................................... 09002967

(51) Int. Cl.
*B08B 3/04* (2006.01)
*A61C 19/00* (2006.01)
*B08B 9/032* (2006.01)
*A61B 19/00* (2006.01)
*A61B 19/02* (2006.01)
*A61B 1/00* (2006.01)
*A61B 1/12* (2006.01)

(52) U.S. Cl.
CPC .............. *A61C 19/002* (2013.01); *A61B 19/34* (2013.01); *B08B 3/04* (2013.01); *B08B 9/0321* (2013.01); *A61B 1/00144* (2013.01); *A61B 1/121* (2013.01); *A61B 19/026* (2013.01); *A61B 2019/0267* (2013.01)

(58) Field of Classification Search
CPC ..................... A61C 19/002; A61B 2019/0267; A61B 19/34; A61B 2019/343; B08B 9/0321; B08B 3/04
USPC ................. 422/294; 134/34, 198, 166 R, 200
See application file for complete search history.

(56) References Cited

U.S. PATENT DOCUMENTS

| | | | | |
|---|---|---|---|---|
| 1,817,530 A | * | 8/1931 | Spanel | 422/294 |
| 4,937,046 A | * | 6/1990 | Andersen et al. | 422/34 |
| 5,019,359 A | * | 5/1991 | Kutner et al. | 422/294 |
| 5,041,264 A | * | 8/1991 | Williams | 422/28 |
| 5,171,523 A | * | 12/1992 | Williams | 422/20 |
| 5,227,132 A | | 7/1993 | Andersen et al. | |

(Continued)

FOREIGN PATENT DOCUMENTS

| | | |
|---|---|---|
| EP | 0 300 945 | 1/1989 |
| JP | 62-84736 | 4/1987 |

(Continued)

OTHER PUBLICATIONS

European Search Report for EP09002967 (mailed Aug. 28, 2009).

*Primary Examiner* — Michael Barr
*Assistant Examiner* — Kevin G Lee
(74) *Attorney, Agent, or Firm* — Klarquist Sparkman, LLP

(57) ABSTRACT

A cleaning or care device for cleaning or care of at least one medical instrument, in particular a dental instrument having a cleaning chamber to receive the at least one instrument to be cleaned and having a media feed, through which a cleaning or care agent can be delivered into the cleaning chamber, wherein the cleaning chamber is bordered by a flexible outer shell, so that the volume of the cleaning chamber is variable. The duration of cleaning or care of the instrument is thus shortened, and the quantity of resources required for this, such as cleaning or care agent or energy, is reduced.

22 Claims, 4 Drawing Sheets

(56) References Cited

U.S. PATENT DOCUMENTS

| | | | |
|---|---|---|---|
| 5,552,115 A * | 9/1996 | Malchesky | 422/28 |
| 5,735,609 A * | 4/1998 | Norton | 383/33 |
| 6,162,395 A * | 12/2000 | Kowanko | 422/33 |
| 6,312,645 B1 * | 11/2001 | Lin et al. | 422/33 |
| 6,534,002 B1 * | 3/2003 | Lin et al. | 422/28 |
| 6,594,971 B1 | 7/2003 | Addy et al. | |
| 7,578,320 B2 * | 8/2009 | Borchardt | 141/7 |
| 2004/0081601 A1 * | 4/2004 | Morrissey et al. | 422/294 |
| 2004/0188302 A1 | 9/2004 | Rogers, Jr. | |
| 2005/0147527 A1 * | 7/2005 | Brown et al. | 422/33 |

FOREIGN PATENT DOCUMENTS

| | | |
|---|---|---|
| JP | 2003047646 | 2/2003 |
| WO | 2006/126103 | 11/2006 |

\* cited by examiner

CLEANING OR CARE DEVICE FOR CLEANING OR CARE OF A MEDICAL INSTRUMENT, IN PARTICULAR A DENTAL INSTRUMENT

CROSS REFERENCE TO RELATED APPLICATION

The present application claims priority from pending European Patent Application No. 09002967.9 filed Mar. 3, 2009, which is incorporated herein by reference.

BACKGROUND

1. Field

The present application relates to a cleaning or care device for cleaning or care of at least one medical instrument, in particular a dental instrument, as well as a method for cleaning or care of such an instrument.

2. Description of Prior Art

The patent application WO 2006/126103 A2 describes a container made of plastic or glass, into which an instrument that is to be sterilized or cleaned can be inserted, and which can be connected to a connection device of a treatment chamber of a sterilizer or a cleaning device. The connection device has media lines, so that cleaning media can be dispensed from the connection device into the container and into or onto the instrument to be cleaned.

The advantage of this cleaning system is that it is not necessary to fill the entire treatment chamber with the cleaning agent in order to clean an instrument but instead only the smaller volume of the container must be filled with the cleaning agent. This shortens the duration of the cleaning cycle and reduces the resources such as energy or cleaning media required.

It would be advantageous to create a cleaning or care device for cleaning or care of a medical instrument, in particular a dental instrument, which allows more rapid cleaning or care or a further reduction in the required resources in comparison with the prior art.

SUMMARY

According to one embodiment, this is accomplished by a cleaning or care device for cleaning or care of at least one medical instrument, in particular a dental instrument, comprising a cleaning chamber to hold the at least one instrument to be cleaned and a media feed, which delivers a cleaning or care agent into the cleaning chamber, wherein the cleaning chamber is bordered by a flexible outer shell, so that the volume of the cleaning chamber is variable.

By providing a flexible elastic outer shell and by varying the volume of the cleaning chamber, it is possible to adapt the cleaning chamber to the external form or shape of the instrument to be cleaned in each case. The cleaning chamber thus does not have a rigid shape and does not have a permanent volume, as is known in the prior art, but instead its volume and in particular also its shape are variable. The cleaning chamber preferably adapts to the shape of the respective instrument to be accommodated or it follows the shape of the instrument. Thus according to an especially preferred embodiment, there are no significant voids in the cleaning chamber but instead the volume of the cleaning chamber consists only of the volume of the instrument to be cleaned and a small distance between the instrument and the flexible outer shell. The quantities of resources required for cleaning or care are substantially reduced in this way and at the same time the duration of the cleaning or care is shortened.

The cleaning or care device as described herein is understood to refer to all devices or components of devices which execute or enable a cleaning treatment, for example, with water, with compressed air, with a solvent or a cleaning agent, with a soap solution or by ultrasound, a care treatment (e.g., by introducing a lubricant), a disinfection treatment or a sterilization treatment (e.g., by steam or by ethylene oxide or by some other treatment for removing impurities or microorganisms on a medical or dental instrument). In particular, the cleaning or care device is embodied as a sterilizer, e.g., as a steam sterilizer, as a thermal disinfector or as a chemical disinfector.

Depending on the embodiment, the cleaning or care device may be operated in batch mode, in which the treatment medium remains in the cleaning chamber for a certain period of time, and/or in continuous mode, in which the treatment medium flows continuously through the cleaning chamber without remaining there for an extended period of time.

The instruments to be cleaned may comprise any type of medical devices, in particular dental devices, solid or hollow devices or parts of these devices, e.g., mirrors, tweezers, scissors, forceps, endoscopes, motors, couplings, adapters, handpieces and contra-angle handpieces, saw drives, drills, files, saw blades, trocars, tubes, dishes, shelves, awls, syringes, etc.

According to one embodiment, a device on or connected to the cleaning or care device is effective to induce a change in the volume and/or the shape of the cleaning chamber. This device can be configured, for example, as a delivery device which delivers a first working medium, e.g., a fluid, in particular on the outside of the flexible outer shell. The delivery device comprises, for example, a pump for the working medium, a compressor, lines for delivering the working medium, valves, throttles, switches or other control elements. The delivery device or at least parts thereof may also be used for draining off the working medium, e.g., after completion of the treatment of the instrument.

A gas under pressure, e.g., compressed air, or a liquid, e.g., water, or foam is preferably used as the working medium. The first working medium delivered to the outside of the flexible outer shell expands the outer shell by its pressure or mass in the direction of the instrument to be cleaned, so that the outer shell at least approaches the instrument or comes in contact with it at some locations. If the feed of the first working medium is stopped and/or the first working medium is removed from the outside of the flexible outer shell, then the flexible outer shell preferably retracts from the instrument because of its elasticity or especially preferably returns to its original starting position and to its original shape.

Alternatively or in addition to the aforementioned delivery device, the volume or shape changing device may also include at least one movable mechanical element, e.g., a displaceable piston or pin, which moves the flexible outer shell, preferably by direct contact, in the direction of the instrument and/or away from it. To move the at least one movable mechanical element, it is preferably connected to a drive, e.g., to a pneumatic, hydraulic or electric motor drive. The at least one movable mechanical element is especially preferably designed to be telescoping.

According to one embodiment, the flexible outer shell is directly or indirectly attached to a rigid wall, preferably metallic or made of plastic. The rigid wall is designed, for example, as a chamber or housing, which surrounds the flexible outer shell, in particular as a chamber or housing of a cleaning unit or care unit, e.g., of a sterilizer. Alternatively, the rigid wall is part of a cleaning/care and storage container, which can preferably be introduced into and removed from a cleaning or care unit, e.g., a sterilizer. The interior of the cleaning/care and storage container in this case forms the cleaning/care and storage chamber, into which the instrument for cleaning/care is introduced and in which it is stored until it is used again. The rigid wall is preferably designed here as a container lid of the cleaning/care and storage container.

If the rigid wall surrounds the flexible outer shell, then according to one embodiment, the delivery device for the working medium is positioned at a point between the flexible outer shell and the rigid wall, so that the first working medium can be delivered between the flexible outer shell and the rigid wall. A storage space is thus advantageously created between the rigid wall and the flexible outer shell, so that the first working medium can be introduced into this space and stored there during the treatment of the instrument and then removed again, so that the quantity of the first working medium to be delivered and the energy required for its delivery are reduced. The delivery device for the first working medium may preferably include a cutoff element, e.g., a control valve or a switching tap, which cuts off the storage space from the environment after the storage space is filled with the first working medium, so that the storage space is not filled with the first working medium continuously but instead is filled discontinuously, preferably only once before the start of the treatment of the instrument.

According to one embodiment, the flexible outer shell is formed by an elastic film or by an elastic membrane, in particular made of plastic, rubber or caoutchouc, which is impermeable for fluids, in particular for water and/or steam and/or compressed air and/or microorganisms.

According to a preferred embodiment, the cleaning device or care device includes a spacer device, which prevents the flexible outer shell from coming in contact with the instrument or prevents contact between the instrument and the outer shell or counteracts excessively tight contact between the flexible outer shell and the instrument, so that the treatment medium can flow around the outside or the surface of the instrument. The spacer device can have multiple spacers, for example, which are arranged on the inside of the flexible outer shell, which at the same time forms the inside of the cleaning chamber, and are designed to come in contact at least partially with the instrument to be cleaned. The spacers may be formed by nubs or strips in particular. The spacers are arranged at regular or irregular intervals and prevent the flexible outer shell from coming in contact with the instrument to be cleaned or from coming in contact with it completely.

In order for the treatment medium also to reach the locations on the outside or surface of the instrument which are in contact with the spacers, in an especially preferred embodiment, a device is provided for moving the instrument accommodated in the cleaning chamber in relation to the flexible outer shell. Surface sections of the instrument may of course also be separated from the flexible outer shell by this movement device if the outer shell comes in contact with portions of the instrument. The movement device comprises, for example, a connection piece to which the instrument to be cleaned can be connected or comprise a receptacle into which the instrument to be cleaned can be inserted and which can be pivoted or displaced or induced to rotate or vibrate. The connecting piece is preferably designed as a tubular or peg-shaped coupling element. The connecting piece or the receptacle are connected to a drive for generating the movement, e.g., an electric motor or a vibration generator, optionally via connecting elements such as shafts, gears or vibration conductors.

Alternatively or additionally, the spacer device can comprise a delivery device for a second working medium, e.g., a fluid, opening into the cleaning chamber and introducing the second working medium into the cleaning chamber between the instrument to be cleaned and the flexible outer shell. The second working medium surrounds or flows around the instrument or flows through the cleaning chamber, preferably continuously in each case and thus prevents the flexible outer shell from coming in contact with the instrument at all or too tightly at least at certain times and/or at certain locations on the instrument to be cleaned. The delivery device is designed either as a separate delivery device delivering exclusively the second working medium or it is part of a shared delivery device for delivering the first and second working media or for delivering the second working medium and at least one cleaning or care agent. In the case of a shared delivery device, at least parts of the delivery device, for example, lines, control elements, switch elements, pumps, etc., are used jointly for the second working medium and the other medium.

In addition to the delivery device for the second working medium, the spacer device especially preferably comprises a control device and/or regulating device, which controls or regulates the pressure prevailing in the storage chamber and/or cleaning chamber, such that the flexible outer shell comes in contact with the instrument to be cleaned only partially or not at all. To do so, the control and/or regulating device comprises one or more pressure sensors, such that at least one pressure sensor is arranged in the cleaning chamber and in the storage space. The pressure sensors detect the pressures in the cleaning chamber and in the storage space and conduct corresponding pressure sensor signals to the control and/or regulating device. The control and/or regulating device compares the pressure sensor signals with one another and/or with predetermined pressure comparison values and controls and/or regulates at least one operating parameter of one of the two or both working media, in particular the volume flow and/or the pressure, such that the flexible outer shell does not come in contact with the instrument to be cleaned in at least one location. Alternatively, the control and/or regulating device has other sensors, for example, one or more contact sensors, which detect contact between the instrument and the flexible outer shell, or expansion sensors, each of which is positioned on the flexible outer shell and whose sensor signals serve to control/regulate an operating parameter of at least one of the two working media, as described above.

The control and/or regulating device for delivering the first and/or second working medium and also, if necessary, for removing the first and/or second working medium comprises at least one valve and/or at least one sensor, for example, in particular a pressure sensor or a flow-through sensor and/or at least one microcontroller. The control and/or regulating device preferably also monitors, controls and/or regulates the entire sequence of the cleaning or care process.

A method for cleaning or care of a medical instrument, in particular a dental instrument with a cleaning or care device described above comprises the step of altering the volume of the cleaning chamber after introducing the instrument into the cleaning chamber. To do so, a first working medium, in particular a fluid, is delivered in the direction of or toward the outside of the flexible outer shell. The volume of the cleaning chamber is preferably altered, so that the shape of the cleaning chamber essentially adapts to, follows or conforms to the shape of the instrument, or the flexible outer shell is at least partially in contact with the instrument.

These and additional embodiments are explained in greater detail below on the basis of preferred embodiments and with reference to the accompanying drawings:

DETAILED DESCRIPTION

Figure 1A:
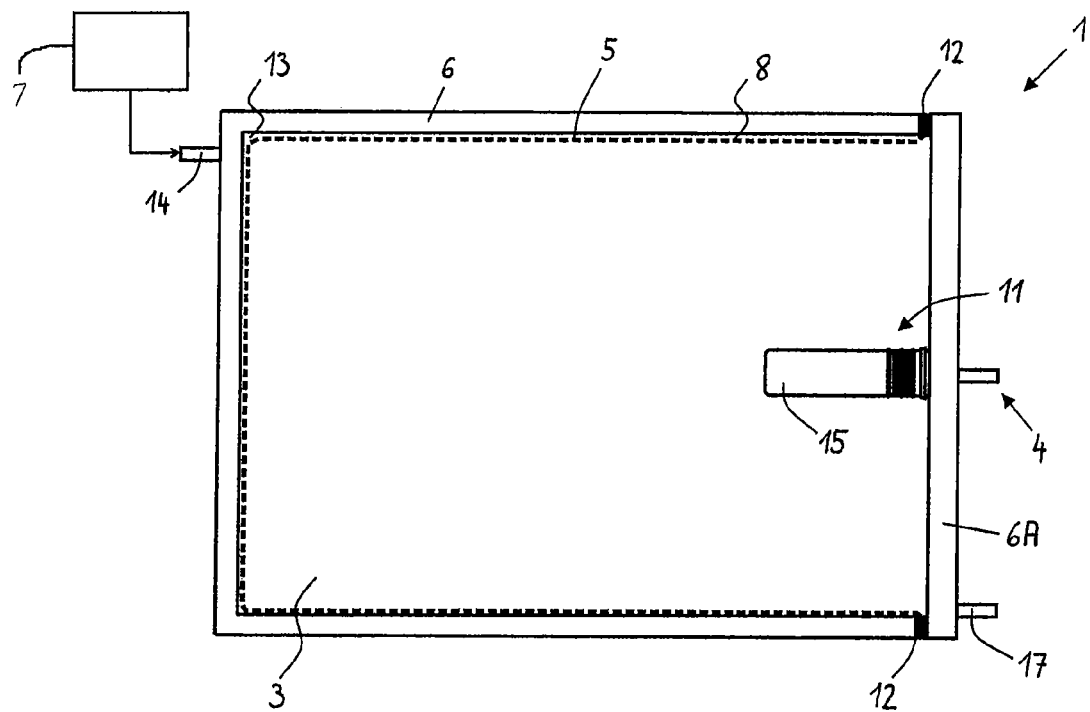
FIGS. 1A and 1B show in schematic diagrams a first embodiment of a cleaning chamber of a cleaning or care device in an empty state (FIG. 1A) and in a loaded state during cleaning or care (FIG. 1B).
Figure 1B:
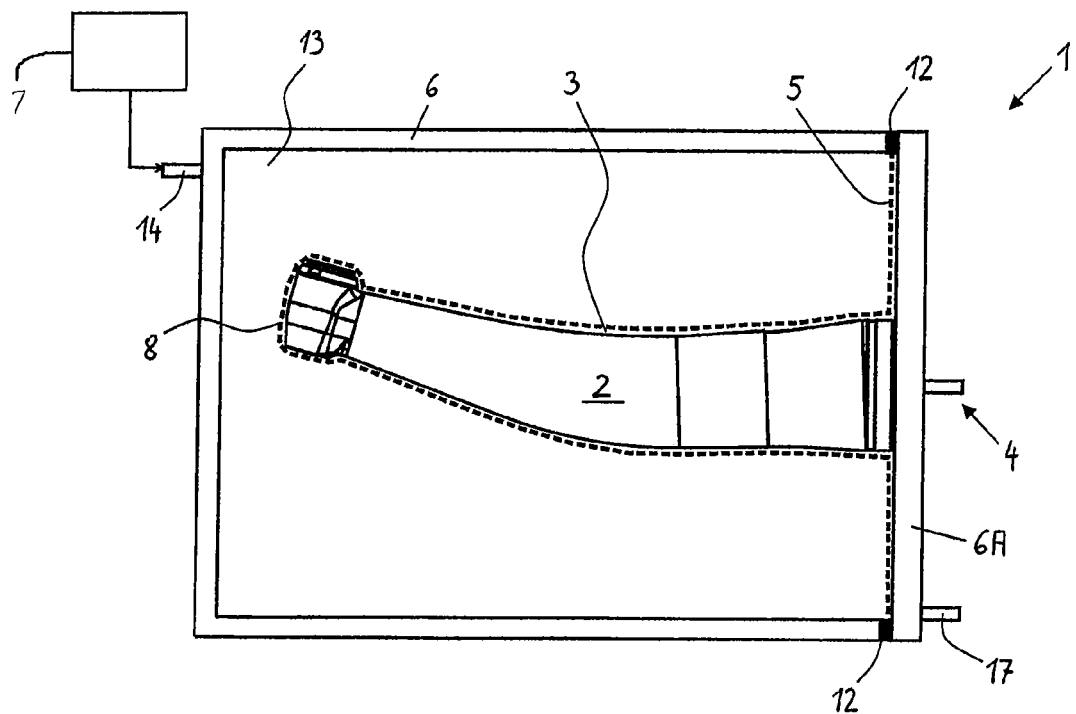

The cleaning or care devices 1, 1' illustrated in FIGS. 1A, 1B, 2A and 2B have multiple rigid, e.g., metallic walls 6, 6', which together form an outer housing of the cleaning or care devices 1, F. A lid 6A, 6'A, which is removable from the remaining housing, or a pivotable door is provided on one side wall, so that one or more instruments 2 to be cleaned can be introduced into or removed from the interior of the housing.

A flexible outer shell 5, 5'A, 5'B is provided in the interior of the housing and is attached at two or more points 12, 12'A, 12'B or connecting sections to fixed components of the cleaning or care device 1, 1', in particular to the inside of the outer housing. However, most of the flexible outer shell 5, 5'A, 5'B is loosely arranged in the housing and is freely movable therein. The flexible outer shell 5, 5'A, 5'B consists either of a single bag-like or cylindrical elastic film or membrane (see FIGS. 1A, 1B) or comprises two or more separate sections 5'A, 5'B, each of which is attached independently of the others to different points 12'A, 12'B in the cleaning or care devices 1, 1' (see FIGS. 2A, 2B).

The space enclosed by the flexible outer shell 5, 5'A, 5'B forms a cleaning chamber 3, 3' into which one or more instruments 2 to be cleaned can be introduced. Because of the flexibility and elasticity of the outer shell 5, 5'A, 5'B, at least the volume and preferably also the shape of the cleaning chamber 3, 3' are variable.

The change in volume or shape of the cleaning chamber 3, 3' is induced by a first working medium, in particular by a fluid, preferably a liquid, which can be delivered via delivery means or a delivery device 7, 7' for delivery of the first working medium into an intermediate space or storage space 13, 13'A, 13'B. At least a portion of the delivery device 7, 7' opens into the storage space 13, 13'A, 13'B. The delivery device 7, 7' includes, for example, a line 14, 14', which passes through the housing of the cleaning or care devices 1, 1', a compressor and pressure regulating or control valves. Due to its pressure, the first working medium delivered into the storage space 13, 13'A, 13'B and thus to the outside 8, 8'A, 8'B of the flexible outer shell 5, 5'A, 5'B produces a change in shape or expansion of the flexible outer shell 5, 5'A, 5'B.

Figure 2A:
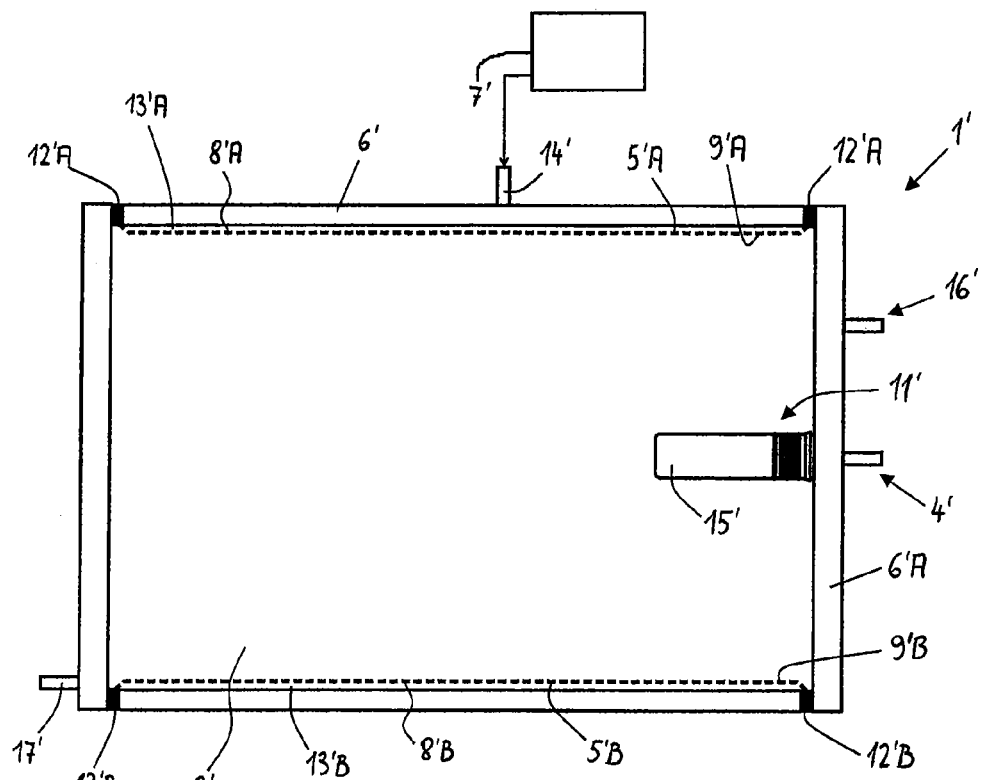
FIGS. 2A and 2B show in schematic diagrams a second embodiment of a cleaning chamber of a cleaning or care device in an empty state (FIG. 2A) and in a loaded state during cleaning or care (FIG. 2B).

FIGS. 1A and 2A show the flexible outer shell 5, 5'A, 5'B in its starting position before delivery of the first working medium. The flexible outer shell 5, 5'A, 5'B extends along the walls 6, 6', so that the cleaning chamber 3, 3' has a much larger volume in comparison with the storage space 13, 13'A, 13'B, preferably assuming its maximum volume, so that convenient insertion of the instrument 2 to be cleaned is ensured for the user.

FIGS. 1A and 2A show the situation after insertion of the instrument 2 into the cleaning or care device 1, 1' and after delivery of the first working medium into the storage space 13, 13'A, 13'B and, if necessary, its closure by a cutoff element, e.g., a valve. The flexible outer shell 5, 5'A, 5'B follows the shape of the instrument 2, so that the volume of the cleaning chamber 3, 3' is reduced and the volume of the storage space 13, 13'A, 13'B is increased. In particular, the proportional volume of the cleaning chamber 3, 3', which is not filled by the instrument 2 and in which a cleaning agent or care agent, e.g., steam or a disinfectant, surrounds the surface of the instrument 2, is significantly reduced, so that the amount of treatment agent required for cleaning or care and the duration of filling of treatment agent into the cleaning chamber 3, 3' or removal of the treatment agent from the cleaning chamber 3, 3' can be reduced to a minimum. This is especially advantageous with sterilizers in which the entire cleaning chamber 3, 3' must be filled with steam several times during a sterilization cycle and then evacuated again.

After completion of the cleaning or care of the instrument 2, the first working medium is drained out of the cleaning chamber 3, 3' via the delivery device 7 or other delivery structure and lines, so that the flexible outer shell 5, 5'A, 5'B essentially returns to its starting position and shape shown in FIGS. 1A, 2A. The storage space 13, 13'A, 13'B and the cleaning chamber 3, 3' thus have a total volume V, which is composed of the volumes V1 of the storage space 13, 13'A, 13'B and V2 of the cleaning chamber 3, 3' which vary during a treatment cycle or care cycle.

In the embodiments according to FIGS. 1A-2B, the instrument 2 is fastened in the cleaning or care device 1, 1' by a rod-shaped plug coupling element 15, 15' which is connected to the wall 6, 6' and can be inserted into a corresponding tubular receptacle of the instrument 2. The plug coupling element 15, 15' is preferably designed as a hollow shaft or includes one or more lines, which are connected to media sources for the cleaning or care agent via the media feed 4, 4', including multiple media lines, for example. The cleaning or care agent is sent into the cleaning chamber 3, 3' via the plug coupling element 15, 15', and if the instrument 2 has cavities, lines, channels, etc., in its interior, which should also be cleaned or maintained, then the cleaning or care agent is also sent directly into the interior of the instrument 2. Instead of the plug coupling element 15, 15', other fastening devices for instruments to be cleaned may of course also be provided, e.g., baskets or receptacles for insertion of the instrument 2.

Figure 2B:
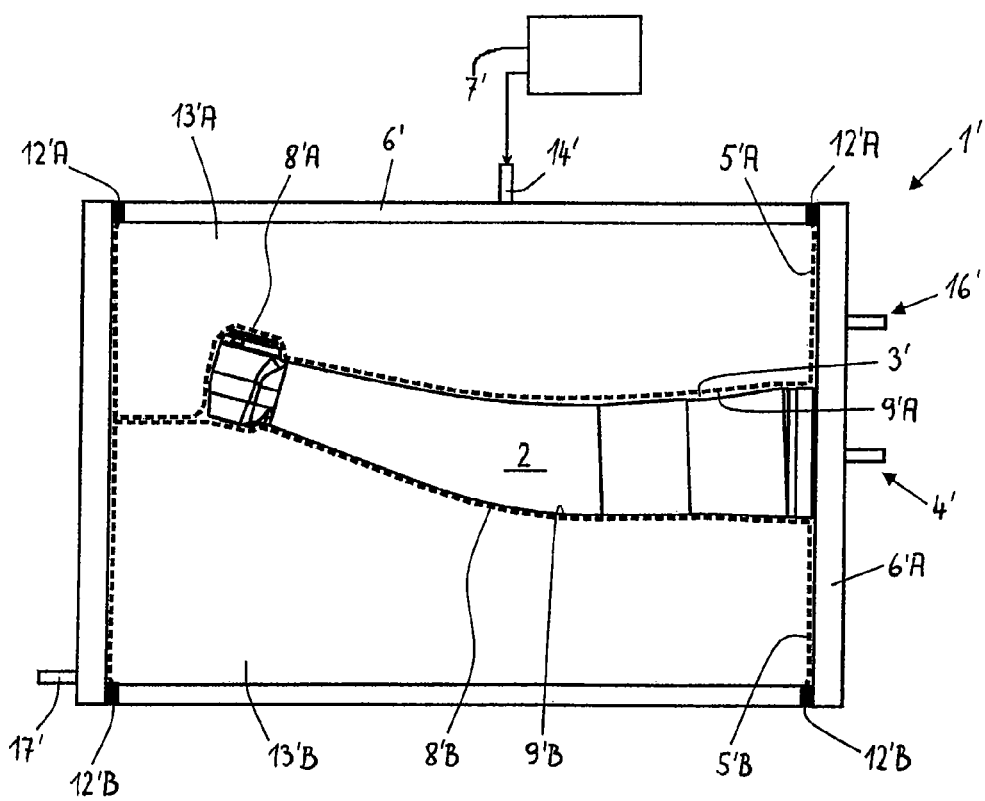

In FIGS. 2A, 2B, the cleaning or care device 1' comprises a second media feed 16' with a media line, which opens directly into the cleaning chamber 3' in addition to or as an alternative to the plug coupling element 15' which serves to supply cleaning or care agent. A cleaning or care agent, which serves in particular to clean or care for the outside of the instrument 2, may be directed into the cleaning chamber 3' through this second media feed 16', which is also connected to a media source. Alternatively or additionally, a second working medium, in particular a fluid, may also be introduced into the cleaning chamber 3' through the second media feed 16', at least partially preventing the flexible outer shell 5'A, 5'B from coming in contact with the instrument 2 or preventing contact between the instrument 2 and the flexible outer shell 5'A, 5'B or counteracting excessively close contact of the flexible outer shell 5'A, 5'B with the instrument 2.

It is naturally also possible to direct the second working medium through the plug coupling element 15, 15' or through corresponding fastening devices for the instrument 2 to the cleaning chamber 3, 3'. In this case either the plug coupling element 15, 15' has a direct connection for the second working medium into the cleaning chamber 3, 3', or the second working medium flows into the cleaning chamber 3, 3' through the instrument 2 and through openings provided on the instrument 2, e.g., the tool receptacle opening or spray openings.

The cleaning or care agents leave the cleaning chamber 3, 3' through a media outlet 17, 17'. The media outlet 17, 17' comprises, for example, a suction pump, control valves or non-return valves, lines or containers for collecting the used treatment media.

Figure 3:
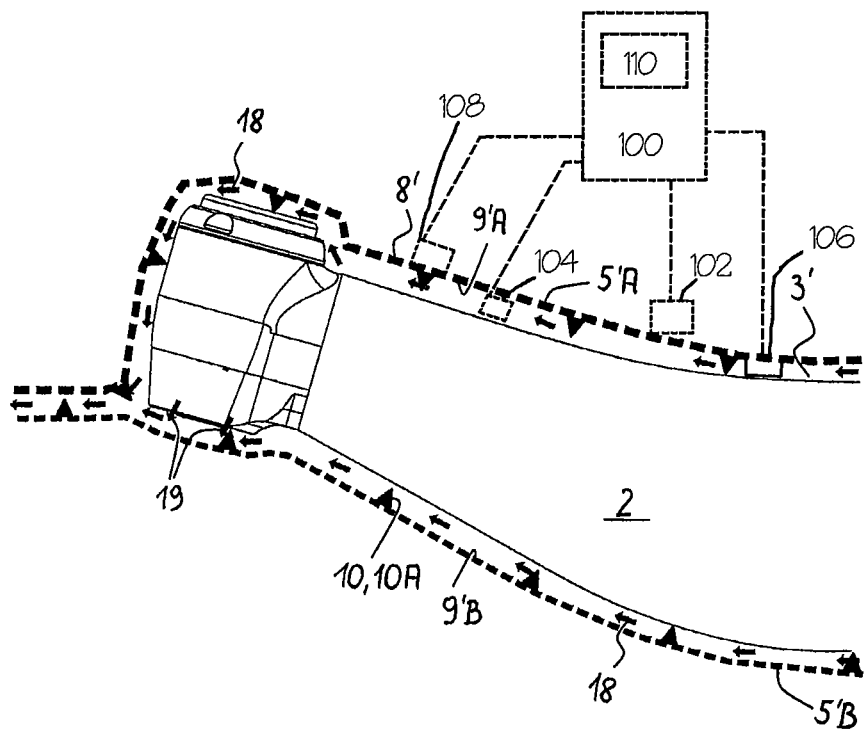
FIG. 3 shows an enlarged detail of FIG. 2B with a portion of the instrument to be cleaned and with the cleaning chamber, which has been adapted in volume and shape to the instrument.

On the basis of the enlarged detail from FIG. 2B shown in FIG. 3, it can be seen that spacers 10 in the form of triangular nubs 10A are provided on the inside 9'A, 9'B of the flexible outer shell 5'A, 5'B. The spacers 10 are preferably an integral part of the flexible outer shell 5'A, 5'B. They prevent the film or membrane of the flexible outer shell 5'A, 5'B from coming in contact with the instrument 2 and thus also allow the flow of cleaning agent or care agent through the cleaning chamber 3' along the outside of the instrument 2, this flow being indicated by the arrows 18. The arrows 19 point to the outlet of cleaning agent or care agent out of the interior of the instrument 2.

In order for those sections of the surface of the instrument 2 which are covered or contacted by the spacers 10 or with which the flexible outer shell 5'A, 5'B is possibly in contact, to come in contact with cleaning agent or care agent, a movement device 11, 11' is additionally provided for moving the instrument 2, which is accommodated in the cleaning chamber 3, 3', in relation to the flexible outer shell 5, 5'A, 5'B. The movement device 11, 11' comprises, in addition to the plug coupling element 15, 15', which is described above and can be induced to rotate or execute a longitudinal movement or vibration or other fastening devices for the instrument 2, e.g., shafts, gears, vibration transmitting elements or a drive for generating the movement, for example, an electric motor or a vibration generator.

Figure 4A:
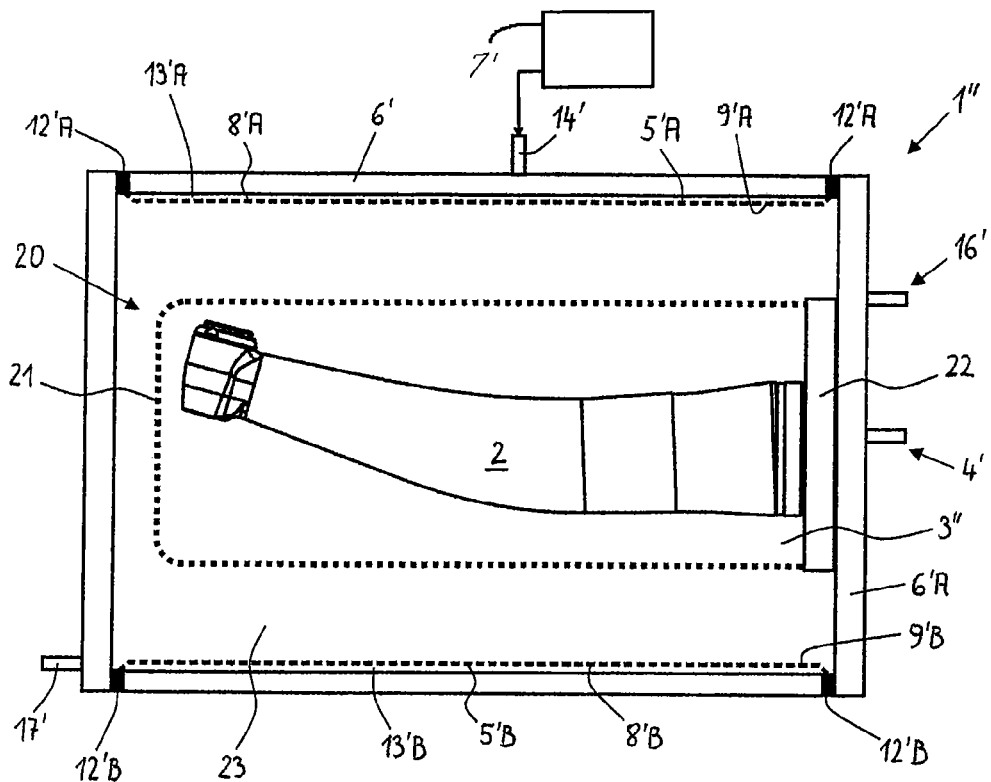
FIGS. 4A and 4B show in schematic diagrams a third embodiment of a cleaning chamber of a cleaning or care device in a loaded state, with a first volume of the cleaning chamber (FIG. 4A) and with a second reduced volume during the cleaning or care of the instrument (FIG. 4B).
Figure 4B:
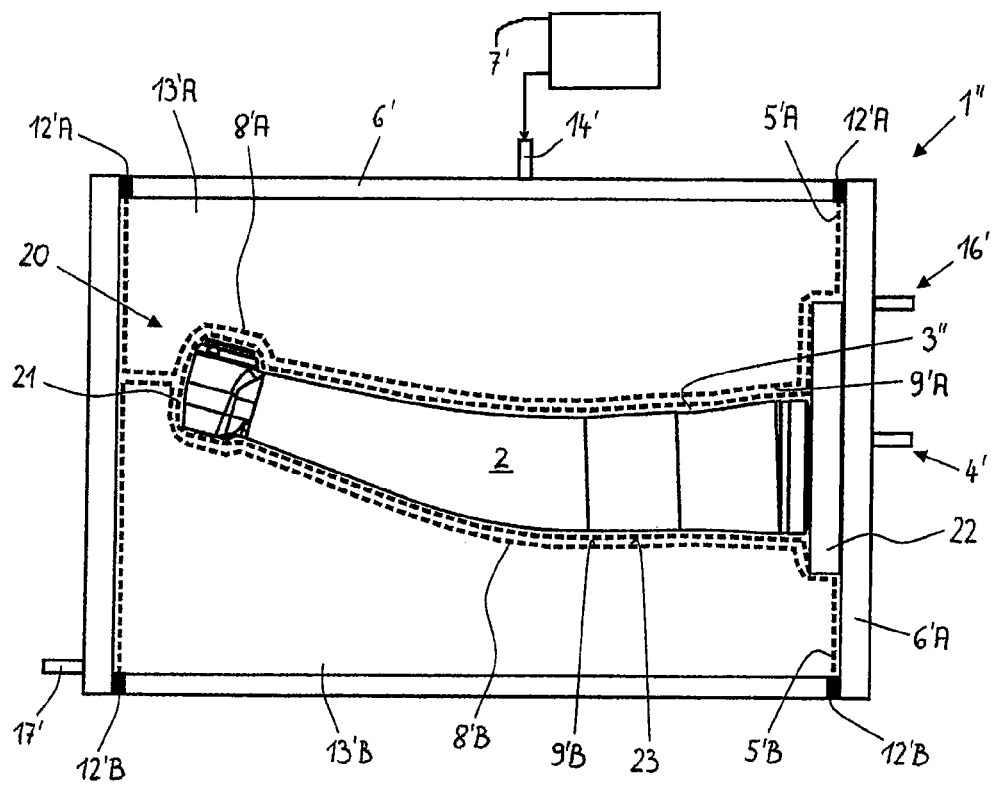

The cleaning or care device 1" according to FIGS. 4A and 4B comprises at least one container 20, preferably in addition to a cleaning or care device, which has essentially the same design as the cleaning or care device 1' of FIGS. 2A, 2B, so that the same components are labeled with the same reference numerals. In contrast with the cleaning or care devices described above, the cleaning chamber 3" of the cleaning or care device 1" is formed by the interior of the container 20, which can be introduced into the cleaning or care device 1" or removed from it. The container 20 comprises an outer wall having a cylindrical shape, for example, and formed at least partially by a flexible outer shell 21 and a lid 22, which can be detachably connected to the outer shell 21.

A fastening device for the instrument 2 to be cleaned, e.g., a plug coupling element 15, 15' as described in FIGS. 1A and 2A, is provided on the inside of the lid 22 facing the cleaning chamber 3". At least one media connection is provided on the outside of the lid 22 facing away from the cleaning chamber 3", the media connection being connected or connectable directly or indirectly via the media feed 4', 16' of the lid 6'A to one or more media sources and also being connected to the fastening device for the instrument 2 that is to be cleaned, so that at least one cleaning or care agent and/or a second working medium can be delivered into the instrument 2 and/or into the cleaning chamber 3". The media delivered into the cleaning chamber 3" are also drained out through media lines passing through the lid 22.

The container 20 thus comprises a cleaning chamber 3" to receive the at least one instrument 2 to be cleaned and a media feed, through which a cleaning or care agent can be delivered into the cleaning chamber 3", wherein the cleaning chamber 3" is bordered by a flexible outer shell 21, so that the volume of the cleaning chamber 3" is variable. As already explained above for the cleaning or care devices 1, 1', the volume of the cleaning chamber 3" is variable due to the flexibility of the outer shell 21 of the container 20. The change in the volume is accomplished in the same way as that described for the cleaning or care device 1', i.e., by introducing a first working medium by means of the delivery device 7' into the storage space 13'A, 13'B, so that the first flexible outer shell 5'A, 5'B is deformed and the volume of the storage space increases until the flexible outer shell 5'A, 5'B comes in contact with the flexible outer shell 21 of the container 20 and displaces or deforms it, so that the volume of the cleaning chamber 3" decreases (see FIG. 4B). By draining out the first working medium out of the storage space 13'A, 13'B, both of the flexible outer shells 21 essentially return to their starting position, preferably automatically.

According to one embodiment, the container 20 has a spacer device for at least partially maintaining a distance of the flexible outer shell 21 from the instrument 2, such that the spacer device comprises spacers, in particular nubs or strips provided on the inside of the flexible outer shell 21 or a delivery device 16' for a second working medium opening into the cleaning chamber 3". The design of this spacer device corresponds to the design of the spacer devices described above.

According to one embodiment, when a gaseous medium, e.g., compressed air, is used as the first working medium in particular, the first flexible outer shell 5'A, 5'B may be omitted, so that the first working medium is delivered by the delivery device 7' directly to the outside of the flexible outer shell 21 of the container 20, preferably by dispensing the first working medium into the interior space 23 of the outer housing formed by the walls 6'.

The advantage of using the container 20 consists in particular of the fact that the container 20 serves not only for storage of the instrument 2 during cleaning or care but also that the instrument 2 can remain in the container 20 after completion of the cleaning or care until its renewed use. The container 20 is thus also a container for protection and storage of the cleaned or maintained instrument 2 because of its impermeability for water and/or steam and/or compressed air and/or microorganisms.

For cleaning or care, the lid 22 is released from the container 20, the instrument 2 is attached to the fastening device provided on the lid 22, e.g., to the plug coupling element 15, 15', and the lid 22 together with the instrument 2 is again attached to the container 20, so that the instrument 2 is accommodated in the interior of the container 20 forming the cleaning chamber 3". Then the container 20 together with the instrument 2 is introduced into the interior space 23 of the cleaning and care device 1' and is connected to the media source(s). After completion of the cleaning or care, in which the volume of the cleaning chamber 3" is altered, the connection of the container 20 to the media sources is separated, the container 20 together with the instrument 2 is removed from the interior space 23 and is stored in sealed form until use of the instrument 2.

As shown schematically in FIG. 3, the cleaning or care device 1, 1' may include an optional control and/or regulating device 100, referred to herein as a "regulating device." The regulating device 100 can be selectively set to regulate the pressure in at least one of the storage chamber 13 and the cleaning chamber 3, such that, e.g., the flexible shell comes into contact with the instrument to be cleaned only partially or not at all. According to one approach, the regulating device 100 comprises at least one pressure sensor 102 configured to measure the pressure in the storage chamber 13. There can be a second pressure sensor 104 configured to measure the pressure in the cleaning chamber 3. The pressure sensor(s) detects the pressure in the surrounding area(s), e.g., in the storage chamber 13 or in the cleaning chamber 3, and causes a corresponding signal to be registered at the regulating device 100. The regulating device 100 processes the signals, e.g., by comparing them with pressure comparison values, and controls and/or regulates at least one parameter, e.g., the volume of flow and/or the pressure, of one or two of the working media so that the flexible shell does not come in contact with the instrument 2 in at least one location. The regulating device 100 can include one or more contact sensors, such as the contact sensor 106 positioned to detect contact between the instrument 2 and the outer shell 5A, 5B. It is also possible to use expansion sensors, such as the sensor 108, flow through sensors and controllable valves, in addition to or instead of other devices, to control and/or regulate an operating parameter of one of the working media.

The regulating device 100 can include a microcontroller 110. The regulating device 100 can be configured to monitor, control and/or regulate one or more steps of the entire sequence of the cleaning or care process.

The present application is not limited to the embodiments described here, but instead includes all embodiments which apply or include fundamentally analogous function principles. In addition, all the features of all the embodiments described and depicted here may be combined with one another.

What is claimed is:

1. A cleaning or care device for cleaning or care of at least one medical or dental instrument, comprising:
   a selectively sizable cleaning chamber shaped to receive the at least one instrument to be cleaned, the cleaning chamber having a flexible outer shell movable in response to mechanical and/or fluid pressure to define a boundary of the cleaning chamber sized for the at least one instrument to be cleaned;
   at least one media feed positioned to selectively deliver a cleaning or care agent into the cleaning chamber;
   a spacer device provided for maintaining a space between the at least one instrument to be cleaned and an inside of the outer shell along and around an entire periphery of the instrument, wherein the spacer device comprises at least one of: spacers which are integral with the flexible outer shell; or a control or regulating device having at least one sensor arranged inside or outside the cleaning chamber to selectively regulate pressure inside or outside the cleaning chamber; and wherein
   the flexible outer shell is directly or indirectly and undetachably fixed to at least one fixed component of the cleaning or care device, wherein the at least one fixed component of the cleaning or care device comprises an outer housing of the cleaning or care device.

2. The cleaning or care device according to claim 1, wherein the flexible outer shell has at least one end attached to the fixed component.

3. The cleaning or care device according to claim 1, further comprising a device for varying the volume of the cleaning chamber which comprises a delivery device for delivery of a working medium sufficient to exert a fluid pressure on the outside of the flexible outer shell.

4. The cleaning or care device according to claim 3, wherein
   the delivery device for delivery of a working medium opens between a rigid wall and the flexible outer shell, so the working medium can be delivered between the rigid wall and the flexible outer shell.

5. The cleaning or care device according to claim 1, wherein
   the flexible outer shell comprises an elastic film or an elastic membrane, wherein said elastic film or an elastic membrane is impermeable for a fluid and/or microorganisms.

6. The cleaning or care device according to claim 1, wherein
   the at least one sensor comprises one of a pressure sensor, a contact sensor, an expansion sensor, and a flow through sensor.

7. The cleaning or care device according to claim 1, wherein
   the spacers which are integral with the flexible outer shell project into an interior of the cleaning chamber.

8. The cleaning or care device according to claim 1, wherein the spacer device further comprises a delivery device for delivery of a second working medium into the cleaning chamber.

9. The cleaning or care device according to claim 1, further comprising a device configured to move the instrument received in the cleaning chamber in relation to the flexible outer shell to separate sections of an outer surface of the instrument from the flexible outer shell and any spacer attached to the outer shell.

10. The cleaning or care device according to claim 1, wherein the control or regulating device is configured to control or regulate delivery of at least one working medium or for removing at least one working medium.

11. The cleaning or care device according to claim 1, wherein
    the cleaning or care device is designed as at least one of a sterilizer, a thermal disinfector and a chemical disinfector.

12. The cleaning or care device according to claim 1, wherein
    the cleaning chamber is formed by the interior space of a container, which can be introduced into and removed from the cleaning or care device.

13. A cleaning or care device for cleaning or care of at least one medical or dental instrument, comprising:
    a selectively sizable cleaning chamber shaped to receive the at least one instrument to be cleaned, the cleaning chamber having a flexible outer shell movable in response to mechanical and/or fluid pressure to define a boundary of the cleaning chamber sized for the at least one instrument to be cleaned; and
    at least one media feed positioned to selectively deliver a cleaning or care agent into the cleaning chamber,
    wherein the flexible outer shell is arranged to border an opening of a fixed component of the cleaning or care device in an empty or unloaded state, so that the at least one medical or dental instrument to be cleaned can be placed into the flexible outer shell attached to the fixed component, and
    wherein the fixed component forms an outer housing of the cleaning or care device, the opening of the fixed component being defined by a wall of the fixed component having an inner surface to which the flexible outer shell is directly or indirectly fixed so that the flexible outer shell is surrounded by the housing and connects to the opening.

14. The cleaning or care device according to claim 13, wherein
a spacer device is provided for maintaining a space between the instrument and an inside of the outer shell along at least a portion of a periphery of the instrument.

15. The cleaning or care device according to claim 14, wherein the spacer device comprises at least one of: spacers which are integral with the flexible outer shell; and a control or regulating device having at least one sensor arranged inside or outside the cleaning chamber to selectively regulate pressure inside or outside the cleaning chamber.

16. The cleaning or care device according to claim 13, wherein
the at least one media feed comprises at least one coupling element which is configured to be inserted into a corresponding tubular receptacle of the at least one instrument to be cleaned and to convey a cleaning or care agent directly into the interior of the at least one instrument to be cleaned.

17. The cleaning or care device according to claim 13, further comprising a device for varying the volume of the cleaning chamber which comprises a delivery device for delivery of a working medium sufficient to exert a fluid pressure on the outside of the flexible outer shell.

18. The cleaning or care device according to claim 13, wherein
the cleaning or care device is designed as at least one of a sterilizer, a thermal disinfector and a chemical disinfector.

19. A cleaning or care device for cleaning or care of at least one medical or dental instrument, comprising:
a selectively sizable cleaning chamber shaped to receive the at least one instrument to be cleaned, the cleaning chamber having a flexible outer shell movable in response to mechanical and/or fluid pressure to define a boundary of the cleaning chamber sized for the at least one instrument to be cleaned; and
at least one first media feed positioned to selectively deliver a cleaning or care agent, wherein the at least one first media feed comprises at least one coupling element which is configured to be inserted into a corresponding tubular receptacle of the at least one instrument to be cleaned and to convey a cleaning or care agent directly into the interior of the at least one instrument to be cleaned, wherein the at least one coupling element is directly or indirectly fixedly attached to an outer housing of the cleaning or care device or to an inside of a lid facing the selectively sizable cleaning chamber, and wherein
the flexible outer shell is undetachably fixed to at least one fixed component of the cleaning or care device, wherein the at least one fixed component of the cleaning or care device comprises the outer housing of the cleaning or care device.

20. The cleaning or care device according to claim 19, wherein
the at least one first media feed is further designed to selectively deliver a cleaning or care agent directly into the cleaning chamber.

21. The cleaning or care device according to claim 19, further comprising
at least one second media feed positioned to selectively deliver a cleaning or care agent directly into the cleaning chamber.

22. The cleaning or care device according to claim 19, wherein
a spacer device is provided for maintaining a space between the instrument and an inside of the outer shell along at least a portion of a periphery of the instrument.

* * * * *